(12) United States Patent
Matloub et al.

(10) Patent No.: US 8,591,940 B2
(45) Date of Patent: *Nov. 26, 2013

(54) METHOD OF TREATING SCAR TISSUE

(75) Inventors: Haitham Matloub, Waukesha, WI (US); Wilfred Lynch, New Glarus, WI (US)

(73) Assignee: New Medical Technology Inc., Northbrook, IL (US)

( * ) Notice: Subject to any disclaimer, the term of this patent is extended or adjusted under 35 U.S.C. 154(b) by 1245 days.

This patent is subject to a terminal disclaimer.

(21) Appl. No.: 11/961,476

(22) Filed: Dec. 20, 2007

(65) Prior Publication Data

US 2008/0241230 A1    Oct. 2, 2008

Related U.S. Application Data

(63) Continuation-in-part of application No. 10/751,189, filed on Jan. 2, 2004, now Pat. No. 7,316,817.

(51) Int. Cl.
| | |
|---|---|
| *A61F 13/00* | (2006.01) |
| *A61K 9/70* | (2006.01) |
| *A61F 13/02* | (2006.01) |
| *A61L 15/16* | (2006.01) |
| *A61L 15/00* | (2006.01) |

(52) U.S. Cl.
USPC ........... 424/449; 424/443; 424/445; 424/446; 424/447; 424/448

(58) Field of Classification Search
None
See application file for complete search history.

(56) References Cited

U.S. PATENT DOCUMENTS

| | | |
|---|---|---|
| 3,927,669 A | 12/1975 | Glatt |
| 4,838,253 A | 6/1989 | Brassington et al. |
| 4,911,916 A | 3/1990 | Cleary |
| 4,921,704 A | 5/1990 | Fabo |
| 5,352,508 A | 10/1994 | Cheong |
| 5,445,604 A | 8/1995 | Lang |
| 5,492,696 A * | 2/1996 | Price et al. .................. 424/417 |
| 5,759,560 A | 6/1998 | Dillon |
| 5,895,656 A | 4/1999 | Hirshowitz et al. |
| 5,919,476 A | 7/1999 | Fischer et al. |
| 6,051,747 A | 4/2000 | Lindqvist et al. |
| 6,159,494 A | 12/2000 | Widgerow et al. |

(Continued)

FOREIGN PATENT DOCUMENTS

| | | |
|---|---|---|
| DE | 2946553 A | 5/1981 |
| WO | WO 98/00117 A1 | 1/1998 |

(Continued)

OTHER PUBLICATIONS

Ahn et al. "Topical silicone gel: Anew treatment for hypertrophic scars", Surgery, Oct. 1989, pp. 781-787.*

(Continued)

*Primary Examiner* — Isis Ghali
(74) *Attorney, Agent, or Firm* — W. Dennis Drehkoff; Kelly & Krause, L.P.

(57) ABSTRACT

A method of treating scar tissue by applying a composite sheet for delivering therapeutic agents to the skin is disclosed. The composite sheet comprises a flexible porous polymer for holding and releasing the therapeutic agent in a polymer enrobing material. Microchannels pass through the polymer enrobing material and flexible porous polymer to promote the release of the therapeutic agent. The composite sheet is capable of releasing the therapeutic agent for periods of about 0 to about 30 days.

23 Claims, 3 Drawing Sheets

(56) References Cited

U.S. PATENT DOCUMENTS

| | | | |
|---|---|---|---|
| 6,183,770 | B1 | 2/2001 | Muchin et al. |
| 6,284,941 | B1 | 9/2001 | Cox et al. |
| 6,326,410 | B1 | 12/2001 | Cheong |
| 6,472,581 | B1 | 10/2002 | Muramatsu et al. |
| 6,572,878 | B1 | 6/2003 | Blaine |
| 2001/0024656 | A1 | 9/2001 | Dillon |
| 2002/0128578 | A1 | 9/2002 | Johnston et al. |
| 2004/0018227 | A1* | 1/2004 | Park et al. .................... 424/445 |
| 2004/0138605 | A1 | 7/2004 | Sigurjonsson et al. |
| 2004/0153040 | A1 | 8/2004 | Martineau |
| 2004/0191281 | A1 | 9/2004 | Becher |
| 2007/0161936 | A1 | 7/2007 | Svetlik |

FOREIGN PATENT DOCUMENTS

| | | |
|---|---|---|
| WO | WO 98/53825 A1 | 12/1998 |
| WO | WO 00/67730 A1 | 11/2000 |
| WO | WO 2005/067499 | 7/2005 |

OTHER PUBLICATIONS

International Search Report for International Application No. PCT/US08/14018, Apr. 21, 2009, 3 pp.

Written Opinion for International Application No. PCT/US08/14018, Apr. 21, 2009, 5 pp.

EP Search Report Communication dated Jan. 7, 2013 Munich Germany 7 pages.

\* cited by examiner

METHOD OF TREATING SCAR TISSUE

CROSS-REFERENCE TO RELATED APPLICATION

The present patent application is a continuation-in-part of U.S. patent application Ser. No. 10/751,189, filed Jan. 2, 2004 now U.S. Pat. No. 7,316,817, which is hereby incorporated herein by reference.

FIELD OF THE INVENTION

This invention relates to an improved method of treating scar tissue, wounds and various dermatological conditions. by delivering therapeutic agents to the skin by the use of an improved device.

BACKGROUND OF THE INVENTION

While the present invention is directed to treating and preventing scar tissue and treating wounds, cuts, burns, photoaged skin, and other dermatological conditions of the skin, a preferred embodiment will be described showing the delivery of therapeutic agents to the skin by a composite sheet for that is applied to the skin surface.

Typically, when the skin is traumatized, cut or burned, scar tissue will form. In some instances the scar tissue may comprise a large area and may become prominent. The scar tissue may discolor or become darkened, become hypertrophic and protrude from the surface of the skin making it more noticeable. It may overgrow the boundaries of the initial area of injury and continue to grow or form a keloid. If the scar tissue happens to cover a joint, the movement of the joint may become restricted and extremely painful.

The severity of the scarring may be affected by many factors including the dimensions of the wound, the blood supply to the wound area, the thickness and color of the skin, and the orientation of the scar. Further, the age of the victim may also affect the scar formation. In younger individuals, this can and may result in larger, thicker scars in comparison to an older individual.

There are several methods available for treating and reducing keloid and hypertrophic scars. Surgical excision has been used for a number of years and has also been proved to be ineffective in a large number of cases due to the recurrence of scar tissue. The surgery requires removal of the scarred skin and rejoining the normal skin in a manner such that the wounded area is less apparent. This type of treatment is fairly expensive, and since it is surgery, there is the possibility of complications.

Dermal abrasion (dermabrasion) is also used to smooth scar tissue by scraping or shaving off the top layers of the skin using surgical devices. The activity is often successful in leveling the irregularities of the surface scars, however, the procedure is painful and multiple treatments may be required. Given that this is a surgical procedure, the concerns raised above are valid and the potential for complications, including hypertrophic and keloid scars still exists.

Other treatments for scar tissue involve the use of injectable fillers such as collagen or fat, which are injected below the depressed scar tissue to elevate it and have it appear to be level with the surrounding skin. Continuous treatments may be required because the results are not always permanent. These agents cannot be used for elevated scars.

Other therapeutic treatments for scar tissue include occlusive dressings, compression therapy, intralesional corticosteroid injections, cryosurgery, radiation therapy, laser therapy and interferon therapy.

Silicone gels in the form of sheets have been widely used in the management of new scar tissue and hypertrophic keloid scarring. The silicone sheets are typically applied with pressure against scar tissue so the formation of hypertrophic scar tissue and attendant coloration can be reduced resulting in a more normal appearance. Typically the silicone sheets are better than traditional bandages because the gel adapts itself to the contours of the body. While the use of silicone dressings may be somewhat effective in the treatment of new scar tissue, the occlusive effects of the silicone sheets may be associated with infection due to the accumulation of microbes on the skin.

U.S. Pat. No. 6,572,878 describes a method for minimizing the appearance of scars comprising the application of a semi-occlusive device to a closed wound on the skin wherein the device comprises one layer of silicone sheet infused with an antioxidant and an antimicrobial. The device is used on the surface of the skin and reapplied daily for up to thirty days.

U.S. Pat. No. 6,472,581 describes a silicone sheet, which is formed by a silicone gel layer with a silicone elastomer layer. The elastomer layer is formed by curing a silicone elastomer composition obtained by adding a silicone cross-linking compound to an additional reaction carrying silicone gel composition.

U.S. Pat. No. 6,159,494 describes a method for treating scars by applying a microporous tape to the scar tissue containing panthenol, which serves as a contact medium for allowing a therapeutic agent to pass there through to the surface of the skin. Typically a hydrating agent is used that is derived from the plant *Bulbine frutesences*.

U.S. Pat. No. 5,919,476 describes a bandage in the form of a reinforced silicone gel sheet for application to scar tissue. The bandage comprises three layers; a tacky skin contacting first layer made from a silicone sheet, a reinforcing second layer comprising a nonliquid permeable mesh fabric support structure having a plurality of holes there-through and a non-tacky bonding third layer which includes the holes and laminates itself to the first layer, thereby securing the second layer between the first and third layer.

U.S. Pat. No. 5,895,656 describes a gas or gel filled silicone bandage made of silicone sheeting. The flexible silicone sheeting or film contains an interior space that may be filled with dry gas or a hydrophobic gel. Since there is reduced electrical resistance in the scar tissue, the use of the hollow space in the bandage may increase the static electrical field or negative charge applied to the scar which could hasten the inhibitory healing process for hypertrophic and keloid scars. To improve the electric field within the hollow space, small pieces of Teflon™ sheeting or silicone beads may be inserted in the hollow space.

U.S. Pat. No. 5,759,560 describes a silicone thermal plastic sheeting for scar treatment which has two layers, a first layer of a therapeutic agent to be placed on to the skin and a second backing layer of a thermoplastic polymer bonded to the first layer to provide a thick shape to the material.

U.S. Pat. No. 6,284,941 describes a bandage for treatment of scar tissue comprising a flexible and breathable member having first and second sides with an adhesive located on the first side and a scar treatment pad attached to the first side of the flexible member. The scar treatment pad comprises a layer of silicone elastomer adhesively attached to the center area of the first side of the flexible member so that the adhesive borders are located on lateral sides of the scar treatment pad. The flexible member is nonocclusive.

The foregoing patents describe methods of applying silicone to the surface of skin for treating scar tissue, however, as previously stated, the devices are typically occlusive, or if they are nonocclusive, do not provide for additional application of therapeutic agents. Therefore, there is a need for a device and method for applying therapeutic agents to the skin and treating scar tissue including minimizing the appearance of hypertrophic and keloid scars.

Therefore, it is an object of the present invention to provide a device or composite sheet for treating scar tissue and various dermatological conditions.

It is another object of the present invention to provide a device or composite sheet for delivering therapeutic agents to the surface of the skin.

It is a further object of the present invention to provide a device, which can be applied to the surface of the skin for long periods of time, up to thirty days.

It is another object of the present invention to provide a device or composite sheet to be applied to the surface of the skin for preventing scar tissue.

It is another object of the present invention to provide a device or composite sheet to be applied to the surface of the skin for treating acute scars.

It is another object of the present invention to provide a polymer foam material for holding and releasing a therapeutic agent encapsulated in a polymer enrobing material which is in contact with the skin which holds and releases the therapeutic agent on to the skin.

It is another object of the present invention to provide a device or composite sheet to be applied to the surface of the skin for the treatment of nontraumatized skin and for the modulation of the scar forming process through all phases of healing.

It is another object of the present invention to provide a device or composite sheet to be applied to photoaged skin.

It is another object of the present invention to provide a device or composite sheet to be applied to open wounds.

It is another object of the present invention is to provide a composite material containing a plurality of microchannels which pass through a polymer enrobing material and a polymer foam material for holding and releasing a therapeutic agent onto the surface of the skin.

Other objects and advantages will become apparent upon reading the specification of the appendant claims.

SUMMARY OF THE INVENTION

The present invention is a method of treating or preventing scar tissue on skin and treating of wounds, burns, photoaged skin, diabetic ulcers, scar tissue, keloids and other dermatological conditions. A composite sheet is applied to the surface of the skin for delivering a therapeutic agent to the skin. The composite sheet comprises a flexible porous polymer foam material for holding and releasing the therapeutic agent and a polymer enrobing material which is in contact with the skin and encapsulates the polymer foam material and holds and releases the agent. A plurality of micro-channels passes through the polymer enrobing material and polymer foam material for holding and releasing the therapeutic agent. The therapeutic agent may be antioxidant, an antibiotic or other medicament or agent that may be topically applied to the skin. The polymer enrobing material is preferably silicone, which is useful for treating scar tissue.

DETAILED DESCRIPTION OF THE PREFERRED EMBODIMENTS

The present invention may be embodied in other specific forms without departing for the spirit or essential attributes thereof, and it is therefore desired that the present embodiment must be considered in all aspects as illustrative and not restrictive, reference being made to the appendant claims rather than to the foregoing description to indicate the scope of the invention.

The method involves the use of a composite sheet for the application of therapeutic agents for preventing and treating scar tissue and other dermatological conditions, including, for example, photoaged skin, burns, wounds, etc. The composite sheet is capable of delivering and releasing various therapeutic agents to the skin When the appropriate therapeutic agent is loaded into the composite sheet, scar tissue and other dermatological conditions can be treated or prevented.

Figure 1:
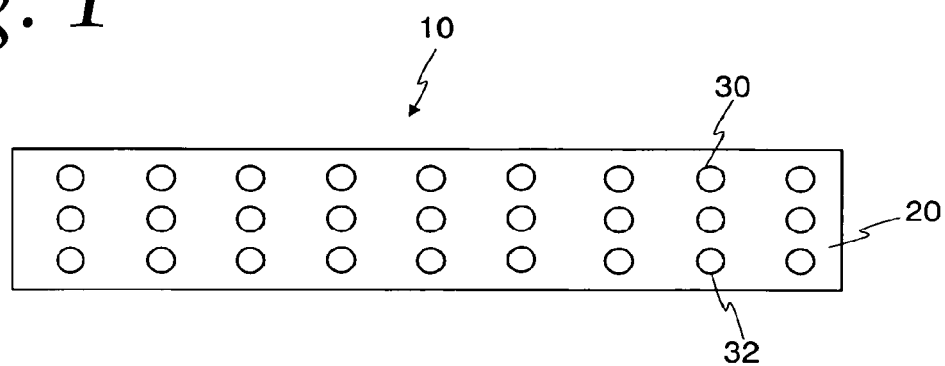
FIG. 1 depicts a top view of the composite sheet material of the present invention.
Figure 2:
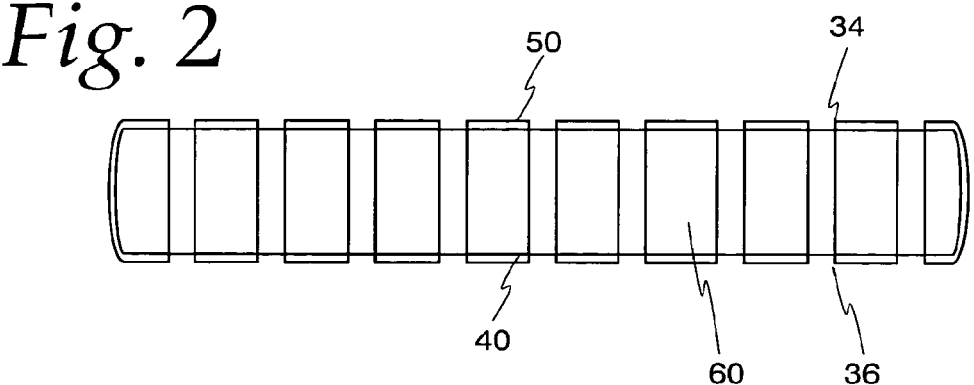
FIG. 2 depicts a length-wise cross-section of the composite sheet material of FIG. 1.
Figure 3:
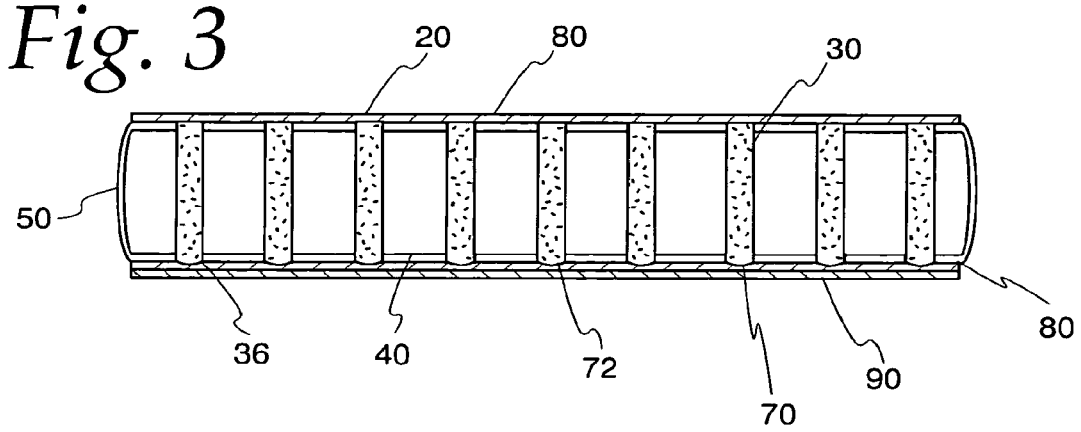
FIG. 3 depicts a cross-section of the composite sheet wherein the therapeutic agents have been added to the microchannels, completely filling the micro-channels.

As seen in FIG. 1, the composite sheet 10 of the present invention comprises a top or first side 20 showing a plurality of apertures or microchannels 30 in the first side 20. The microchannels 30 run from a first aperture 32 on the top side 20 through a porous passage 34, as seen in FIGS. 2 and 3 to a second aperture 36, exiting the second side 40 of the composite sheet of the present invention.

The microchannels 30 pass through a polymer enrobing material 50 which contacts the skin on the second side of the composite sheet and encapsulates a flexible porous polymer foam material 60 that holds and releases a therapeutic agent 70. The polymer enrobing material 50 preferably is a silicone gel or silicone elastomer that is prepared in the form of a sheet. The silicone is soft, durable and of a medical grade. It is impregnated with a therapeutic agent 70, which also passes through the microchannel 30 and into the flexible porous foam material 60. The polymer enrobing material 50 may also be a hydrogel or other suitable material such as ethylene-vinyl acetate and polyurethane elastomers. The therapeutic agent may be released to the skin through the microchannels 30 or through the foam material 60. Typically, a quicker release time is apparent when microchannels 30 are loaded.

Conventional hydrogels can be utilized in accordance with the composite sheet of the present invention. Hydrogels are three dimensional hydrophilic polymer networks capable of swelling in water or biological fluids, and retaining a large amount of fluids in the swollen state. Their ability to absorb water is due to the presence of hydrophilic groups such as —OH, —CONH—, —CONH$_2$, —COOH, and —SO$_3$H. The water content in the hydrogels affects different properties like permeability, mechanical properties, surface properties, and biocompatibility. Hydrogels have similar physical properties as that of living tissue, and this similarity is due to the high water content, soft and rubbery consistency, and low interfacial tension with water or biological fluids. The ability of molecules of different size to diffuse into (drug loading), and out (release drug) of hydrogels, permit the use of hydrogels as delivery systems. Since hydrogels have high permeability for water soluble drugs and proteins, the most common mechanism of drug release in the hydrogel system, is diffusion. Factors like polymer composition, water content, crosslinking density, and crystallinity, can be used to control the release rate and release mechanism from hydrogels.

Hydrogels, based on their nature, can be classified as pH sensitive, temperature sensitive, enzyme sensitive, and electrical sensitive. pH sensitive hydrogels can be neutral or ionic in nature. The anionic hydrogels contain negatively charged moieties, cationic networks contain positively charged moieties, and neutral networks contain both positively and negatively charged moieties. In neutral hydrogels, the driving force for swelling arises from the water-polymer thermodynamic mixing contributions, and elastic polymer contributions. In ionic hydrogels, the swelling is due to the previous two contributions, as well as ionic interactions between charged polymer and free ions. The presence of ionizable functional groups like carboxylic acid, sulfonic acid or amine groups, renders the polymer more hydrophilic, and results in high water uptake.

In the case of anionic polymeric network containing carboxylic or sulphonic acid groups, ionization takes place, as the pH of the external swelling medium rises above the pKa of that ionizable moiety.

The best example for hydrogel is: preparation of poly(2-hydroxyethyl methacrylate) hydrogels from hydroxyethyl methacrylate, using ethylene glycol dimethacrylate as crosslinking agent. Using the above method, a great variety of hydrogels have been synthesized. The hydrogels can be made pH-sensitive or temperature-sensitive, by incorporating methacrylic acid, or N-isopropylacrylamide, as monomers.

Polymers containing functional groups like —OH, —COOH, —$NH_2$, are soluble in water. The presence of these functional groups on the polymer chain, can be used to prepare hydrogels by forming covalent linkages between the polymer chains and complementary reactivity, such as amine-carboxylic acid, isocyanate-OH/$NH_2$ or by Schiff base formation.

Gluteraldehyde can be used as a crosslinking agent to prepare hydrogels of polymers containing —OH groups like poly(vinyl alcohol). Also, polymers containing amine groups (albumin, gelatin, polysaccharides), can be crosslinked using gluteraldehyde.

Polymers that are water soluble, can be converted to hydrogels, using big or higher functional crosslinking agents like divinylsulfone, and 1,6-hexanedibromide. The crosslinking agents react with the functional groups present on the polymer, via addition reaction. These crosslinking agents are highly toxic, and hence unreacted agents have to be extracted. Moreover the reaction has to be carried out in organic solvent, as water can react with the crosslinking agent. The drugs have to be loaded after the hydrogels are formed, as a result the release will be typically first order.

Crosslinking between polymers through hydrogen bond formation occurs as in the case of poly(methacrylic acid) and poly(ethylene glycol). The hydrogen bond formation takes place between the oxygen of poly(ethylene glycol) and carboxylic acid group of poly(methacrylic acid). Carriers consisting of networks of poly(methacrylic acid-g-ethylene glycol) showed pH dependent swelling due to the reversible formation of interpolymer complex, stabilized by hydrogen bonding between the etheric groups of the grafted poly(ethylene glycol), and the carboxylic acid protons of the poly (methacrylic acid).

Most of the covalent crosslinking agents are known to be toxic, even in small traces. A method to overcome this problem and to avoid a purification step, is to prepare hydrogels by reversible ionic crosslinking. Chitosan, a polycationic polymer can react with positively charged components, either ions or molecules, forming a network through ionic bridges between the polymeric chains. Among anionic molecules, phosphate bearing groups, particularly sodium tripolyphosphate is widely studied. Ionic crosslinking is a simple and mild procedure. In contrast to covalent crosslinking, no auxiliary molecules such as catalysts are required. Chitosan is also known to form polyelectrolyte complex with poly (acrylic acid). The polyelectrolyte complex undergoes slow erosion, which gives a more biodegradable material than covalently crosslinked hydrogels.

Figure 5:
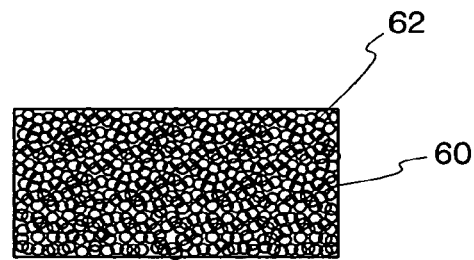
FIG. 5 depicts the open cell structures of the porous polymer foam material.

The flexible porous polymer 60 foam material may be a polymer foam that is flexible, with open foam cells 62 of about 200 to about 300 microns diameter to allow for the holding and releasing of a therapeutic agent, as shown in FIG. 5. Indeed, the open cells of the polymer foam of the present invention should be of a sufficient size to hold an amount of therapeutic active agent so it can be released onto the skin through the polymer enrobing material for as much as about 14 to about 30 days. The polymer foam material may be selected from the group consisting of polyurethane, polyvinylacetate, butyl, polyvinyl alcohol (PVA), polyethylene and medical grade silicone. Preferably hydrophilic polyurethane is utilized. It is available from the following sources: Rynel, Inc. Boothbay, Me. and Lendell Inc. (LMI) St. Charles, Mo.

The thickness of its composite sheet is not critical, however, it typically may have a thickness ranging from about 1 to about 1.5 mm. The flexible polymer foam may have a thickness of about 0.8 to about 0.9 mm.

The density of the foam particle may range from about 0.5 to 9.8 PCF (lbs/cubic feet). Preferably, the density may range from about 0.5 to about 1.5 PCF. The lower the density, the higher the number of air chambers of cells in the foam. More fluid is absorbed when more air chambers or open cells are present in the foam.

The open cell size of the polyurethane or polyvinyl chloride foam is the average diameter of the cells in the final foam product measured in microns. Typically, the size ranges from about 350 to 1,200 microns.

FIG. 2 shows a cross-sectional view of FIG. 1 wherein the microchannels 30 are formed, passing through the first side 20 to second side 40 of the composite sheet material via first aperture 32, porous passage 34 to second aperture 36. The enrobing polymer 50 is shown encapsulating flexible porous foam 60.

FIG. 3 shows a composite sheet that has microchannels 30 filled with a therapeutic agent 70. The microchannels are filled completely so that the therapeutic agent 70 reaches the second aperture 36. The therapeutic agent may flow downward past the second aperture 36 to collect in bulge 72.

If needed, a thin polymer membrane liner 80 may be utilized to cover apertures 32 and 36 on first and second sides 20 and 40, respectively. The liner can be any polymeric material that could be removably attached to the first and second sides 20 and 40 of the composite sheet material. Tire polymeric material may be selected from the group consisting of polyethylene terephthalate, polyethylene terephthalate amorphous, polyethylene terephthalate glycol (glycol modifiers of polyethylene terephthalate), polyvinyl chloride, polypropylene, polystyrene, and polyethylene. Preferably polypropylene is used.

Further, a rigid polymer strip 90 may be applied to either side of the composite sheet, however, preferably it is applied on the second side 40 to cover the polymer liner 80 over apertures 32 and 36. The strip 90 may or may not have raised protrusions 92 to aid the blockage of the therapeutic agent 70 in the microchannels 30, preferably on the second side that contacts the skin of the patient. The strip 90 is removably attached from the first and second sides 20 and 40 prior to application of the composite sheet to the skin. The strip 90 is shown on second side 40 in FIGS. 3 and 4.

Figure 4:
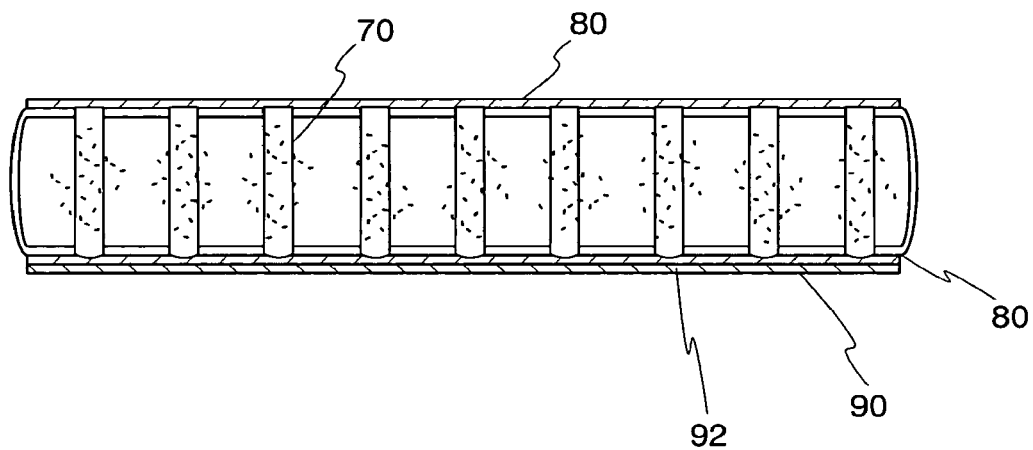
FIG. 4 depicts a cross-section of the composite sheet wherein the therapeutic material has been added to the microchannels and has been dispersed into the porous polymer foam material and polymer enrobing material.

FIG. 4 shows the therapeutic agent 70 filling or partially filling the open cells of the polymer foam 60 into the flexible polymer foam 60 and polymer enrobing material 50 from the microchannels 30. The therapeutic agent easily migrates throughout the foam (due to the open-cell foam properties) and enrobing material. The open foam cells 62 are filled, or partially filled with the therapeutic agent 70 and are ready to release the therapeutic agent into the skin when the strip 90 and liner 80 are removed and the composite sheet is applied to the skin. Typically, when silicone is used as the polymer enrobing material, it will adhere to its skin surface because of its tacky nature.

If necessary, or possibly if other enrobing materials are utilized in the present invention, the appropriate adhesive materials, tapes, bandages, etc. may be used in conjunction with the composite strip to attach the strip to the skin.

FIG. 5 closely shows the open cell 62 of the flexible polymer foam 60.

The therapeutic and nontherapeutic agents which may be utilized with the polymer enrobing material and flexible polymer foam material of the present invention may be any agent that would be suitable for topical application to the skin. For convenience, the term "therapeutic agent" is utilized herein with no intention to be limitative. Hence this device can be used to treat, modulate or prevent various cosmetic or non-cosmetic conditions, diseases, neoplasms, blemishes, photoaged skin, biologic deficiencies, nutritional deficiencies, wounds and scars. More than one therapeutic agent may be utilized. These agents may be drugs, pirfenedine, antibiotics, vitamins, minerals, manufactured substances, interferon, hormones, steroids, natural products or a combination of these and others. For example, antioxidants, and antimicrobials may be loaded into microchannels 30 for release into the flexible foam material 60 and enrobing material 50 for release onto the skin surface. Antioxidants are capable of inhibiting oxidation and when used on the surface of the skin, may prevent fibrosis and decreasing free radical formation when treating wounds and scar tissue. Vitamin E (alpha-tocopherol) is a preferred antioxidant for use in the composite sheet, however, other antioxidants or vitamins may also be utilized, such as vitamin C, ascorbyl palmitate, butylated hydroxyanisole, butylated hydroxytoluene and sodium bisulfate or therapeutic oils and plant or animal extracts such as aloe, emu oil, lavender oil, and rosehip oil. The amount of the antioxidant or other agent used is an amount sufficient to partly or completely fill the open foam cells 62 so that the antioxidant would be released in a time period ranging from zero to about 14 or from about 30 days onto or into the skin. The amount cannot exceed the concentration that will go into and remain in the solution with silicone, if silicone is used as the polymer enrobing material. If other materials are used as the polymer enrobing material, they will determine the amount of therapeutic agent or additive. The amount of antioxidant that may be used in the present invention, when silicone is used as the enrobing material may typically range from about 1% to about 10% by weight of the sheet, with about 1.5% to about 5% being preferred. The composite sheet of the present invention allows for the application of medication to the skin or scar tissue for long periods of time without the need for changing dressings.

Amimicrobials may also be loaded or filled into the microchannels of the present invention. Both the antimicrobials and antioxidants may reach the skin through the microchannels 30 or through the flexible porous foam material 60 and polymer enrobing material 50. Both of these materials may impregnate or be impregnated into the silicone or other enrobing material for release onto or into the skin. The preferred antimicrobial used as a therapeutic agent is polymixin B sulfate. Other antimicrobials, antivirals, antibiotics, antifungals, and antineoplastic agents may also be used in the present invention if they are safe for topical application to the skin and are compatible with other ingredients of the composite sheet material. Examples of these include fusidic acid, bacitracin zinc, gramicidin, silver in various forms and compounds, aminoglycosides, and sulfa based antibiotics such as silver sulphadine.

The antimicrobials allow the composite sheet to remain on the surface of the skin for extended periods of time because they inhibit bacterial growth and treat infections.

Analgesics can be added to this device for the treatment, control or modulation of painful conditions of the skin or other organs and body systems. Similarly, agents for treating global endocrine and nonendocrine deficiencies can be delivered with this device through the skin for management of a variety of conditions, diseases or deficiencies, for example, platelet derived growth factor.

Steroids, for example, corticosteroids selected from the group consisting of triamcinolone and dexamethasone, may also be delivered to the skin by the present invention.

The composite sheet of the present invention may be manufactured by the following steps: (1) pouring the enrobing material, for example, silicone into a mold, (2) adding the flexible porous foam material to the silicone or enrobing material, (3) adding additional silicone or enrobing material to cover the flexible porous foam, (4) curing the silicone mixture or enrobing material by the application of heat, (5) removing the composite sheet material from the mold, (G) cutting holes or apertures through the composite sheet material to form a plurality of microchannels throughout the material by conventional means, (7) loading the microchannels with one or more therapeutic agent, (8) applying a polymer liner to cover the apertures containing the therapeutic agent, and (9) covering the liner with a rigid polymer strip for securely retaining the therapeutic agent in the microchannels of the composite sheet.

For the application to the patient, the composite sheet should be applied to the site to be treated on the skin, for example, scar tissue, wounds, etc. The sheet may be secured if the enrobing material is not sufficiently tacky or sticky for adhesion to the skin. The composite sheet does not have to be applied with much pressure or too tightly, for skin irritation may result. The composite sheet material may stay on the skin of the patient for long periods of time, for example, up to 30 days without reapplication. The sheet materials may be removed from the skin so the patient may cleanse the area and reapplied. The composite sheet can be re-loaded with therapeutic agent after the initial dose of therapeutic agent has been released by inserting additional therapeutic agents into the microchannels. In this manner the composite sheet may be utilized for long periods of time, for example, over 30 days and up to 60 days or more. Further, the composite sheet may be used for 0 to about 14 days or 0 to about 30 days or more. Zero time means that the therapeutic agent may be delivered to the skin through the microchannels immediately upon contact. The antimicrobial agent is typically used in addition with a second therapeutic agent to prevent infection at the site. Nevertheless, the treatment site can be washed with soap and water around the composite sheet to lessen the chances of infection.

Figure 6:
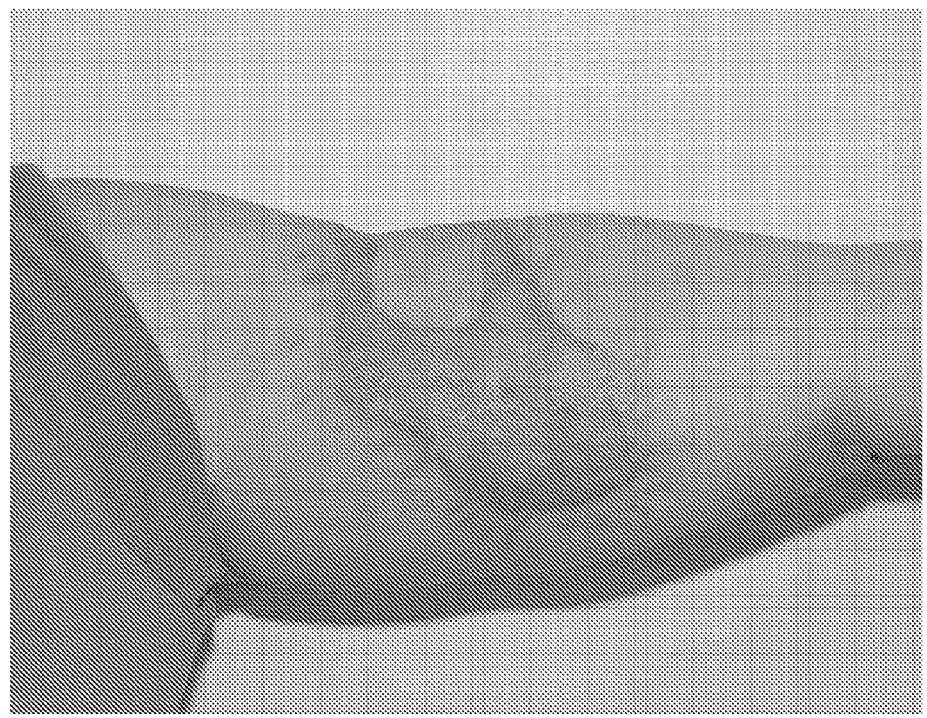
FIG. 6 is a photograph of a subject with scar tissue present before the application of the composite sheet of the present invention.
Figure 7:
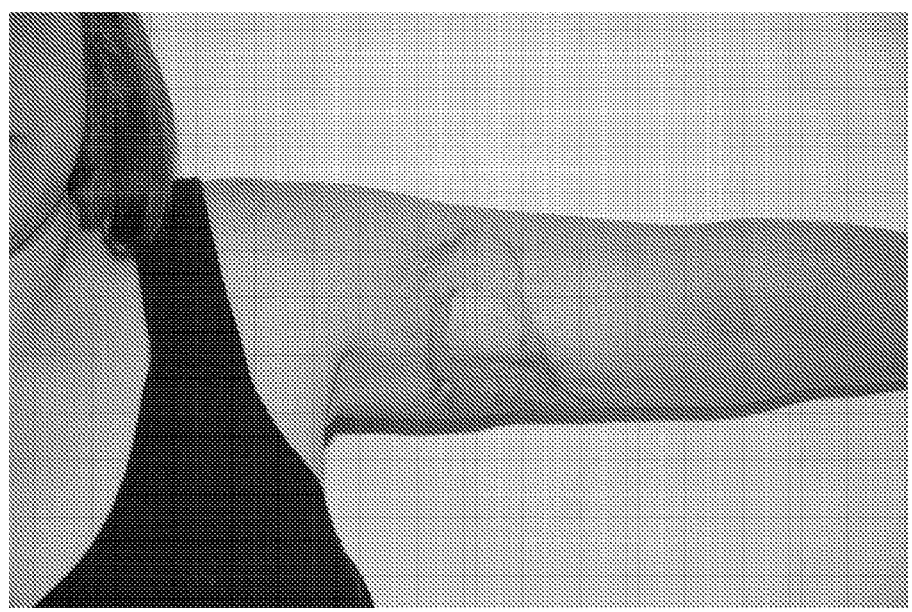
FIG. 7 is a photograph of scar tissue of the subject after administration of the composite sheet of the present invention for 30 days.

The efficacy of the method of the present invention is shown in FIGS. 6 and 7. A 44-year-old female was bitten by a horse on her anterior medial left upper arm, causing an avulsion injury with complete loss of skin and soft tissue down to the fascia. The wound was grafted with split thickness skin graft. FIG. 6 shows the wound approximately 60 days after surgery. The scar tissue is hypertrophic, exhibiting a rough, red surface. The composite sheet of the present invention containing a polyurethane open cell foam layer and an enrobing layer containing medical grade silicone was applied to the scar tissue. The microchannels passing through the layers were filled with Vitamin E for release and distribution to the skin. After 30 days, the resultant improvement in the scar tissue is seen in FIG. 7. The skin surface is smooth and generally normal in color.

Although this invention has been described with reference to a preferred embodiment, obvious modifications and alterations of the invention may be made without departing from the spirit and scope of the invention. The preferred application of the present invention is for the treatment of scar tissue, however, the composite sheet of the present invention may be used for delivering various therapeutic agents to the skin.

What is claimed is:

1. A method of treating scar tissue on human skin comprising:
    applying to the scar tissue a composite sheet including:
        a flexible porous polymer open cell foam material holding a therapeutic agent for release to the skin, the porous polymer open cell foam material selected from the group consisting of polyurethane, polyvinylacetate, polyvinyl alcohol and polyethylene,
        a polymer enrobing material that is in contact with the skin and encapsulates the polymer open cell foam material and holds and releases a therapeutic agent, the enrobing material selected from the group consisting of silicone, hydrogels, ethylene-vinyl acetate and polyurethane elastomers, and
        a plurality of microchannels passing therethrough the polymer enrobing material and polymer open cell foam material for holding and releasing the therapeutic agent wherein the microchannels are loaded with therapeutic agent, and
    the therapeutic agent is released from the porous open cell foam material and delivered from the microchannels to the skin and into the porous open cell foam material and polymer enrobing material for release to the skin.

2. The method according to claim 1, wherein the sheet is applied to the surface of the skin for about 0 to about 30 days.

3. The method according to claim 1, wherein the sheet is applied to the surface of the skin for about 0 to about 14 days.

4. The method according to claim 1, wherein the sheet is applied to the surface of the skin for up to 60 days.

5. The method according to claim 1, wherein the composite sheet is applied to the affected skin surface immediately after surgery to treat scarring of the skin.

6. The method according to claim 1, wherein the plurality of microchannels are loaded with one or more therapeutic agents for releasing the therapeutic agent onto the skin.

7. A method of treating dermatological conditions on human skin comprising:
    applying to the skin a composite sheet including:
        a flexible porous polymer open cell foam material holding a therapeutic agent for release to the skin, the porous polymer open cell foam material selected from the group consisting of polyurethane, polyvinylacetate, polyvinyl alcohol and polyethylene,
        a polymer enrobing material that is in contact with the skin and encapsulates the polymer open cell foam material and holds and releases a therapeutic agent, the enrobing material selected from the group consisting of silicone, hydrogels, ethylene-vinyl acetate and polyurethane elastomers, and
        a plurality of microchannels passing therethrough the polymer enrobing material and polymer open cell foam material for holding and releasing the therapeutic agent wherein the microchannels are loaded with therapeutic agent, and
    the therapeutic agent is released from the porous open cell foam material and is delivered from the microchannels to the skin and into the porous open cell foam material and polymer enrobing material for release to the skin, and wherein the composite sheet is applied to the skin to treat burns, photoaged skin, diabetic ulcers, and wounds.

8. The method according to claim 7, wherein the sheet is applied to the surface of the skin for about 0 to about 30 days.

9. The method according to claim 7 wherein the sheet is applied to the surface of the skin for about 0 to about 14 days.

10. The method according to claim 7 wherein the sheet is applied to the surface of the skin for up to 60 days.

11. The method according to claim 7, wherein the plurality of microchannels are loaded with one or more therapeutic agents for releasing the therapeutic agent onto the skin.

12. The method according to claim 1 wherein the therapeutic agent is an antibiotic selected from the group consisting of polymixin B sulphate, fusidic acid, bacitracin zinc, gramicidin, silver, aminoglycosides and silver sulphadiazine.

13. The method according to claim 1 wherein the therapeutic agent is an antioxidant selected from the group consisting of vitamin E, vitamin E, vitamin C, ascorbyl palmitate, butylated hydroxyanisole, butylated hydroxytoluene and sodium bisulfate.

14. The method according to claim 1 wherein the therapeutic agent is a therapeutic oil selected from the group consisting of lavender oil, rose hip oil, and emu oil.

15. The method according to claim 1 wherein the therapeutic agent is an hormone.

16. The method according to claim 1 wherein the therapeutic agent is a steroid selected from the group consisting of corticosteroids, triamcinolone and dexamethasone.

17. The method according to claim 7 wherein the therapeutic agent is an antibiotic selected from the group consisting of polymixin B sulphate, fusidic acid, bacitracin zinc, gramicidin, silver, aminoglycosides and silver sulphadiazine.

18. The method according to claim 7 wherein the therapeutic agent is an antioxidant selected from the group consisting of vitamin E, vitamin E, vitamin C, ascorbyl palmitate, butylated hydroxyanisole, butylated hydroxytoluene and sodium bisulfate.

19. The method according to claim 7 wherein the therapeutic agent is a therapeutic oil selected from the group consisting of lavender oil, rose hip oil, and emu oil.

20. The method according to claim 7 wherein the therapeutic agent is an hormone.

21. The method according to claim 7 wherein the therapeutic agent is a steroid selected from the group consisting of corticosteroids, triamcinolone and dexamethasone.

22. The method according to claim 1, wherein the therapeutic agent is a pharmaceutical selected from the group consisting of platelet-derived growth factor, pirfenedine, and interferon.

23. The method according to claim 7 wherein the therapeutic agent is a pharmaceutical selected from the group consisting of platelet-derived growth factor, pirfenedine, and interferon.

* * * * *